(12) United States Patent
Reiber et al.

(10) Patent No.: US 10,740,961 B2
(45) Date of Patent: Aug. 11, 2020

(54) METHOD AND APPARATUS FOR RECONSTRUCTING A THREE-DIMENSIONAL REPRESENTATION OF A TARGET VOLUME INSIDE AN ANIMAL OR HUMAN BODY

(71) Applicant: MEDIS ASSOCIATED B.V. [NL/NL], Leiden (NL)

(72) Inventors: Johan Hendrikus Christiaan Reiber, Leiden (NL); Johannes Petrus Janssen, Leiden (NL); Gerhard Koning, Leiden (NL); Shengxian Tu, Leiden (NL)

(73) Assignee: Medis Associated B.V., Leiden (NL)

( * ) Notice: Subject to any disclaimer, the term of this patent is extended or adjusted under 35 U.S.C. 154(b) by 24 days.

(21) Appl. No.: 16/302,373

(22) PCT Filed: May 17, 2017

(86) PCT No.: PCT/NL2017/050310
§ 371 (c)(1),
(2) Date: Nov. 16, 2018

(87) PCT Pub. No.: WO2017/200381
PCT Pub. Date: Nov. 23, 2017

(65) Prior Publication Data
US 2019/0295316 A1  Sep. 26, 2019

(30) Foreign Application Priority Data
May 17, 2016 (NL) .................................. 2016787

(51) Int. Cl.
*G06T 17/00* (2006.01)
*A61B 6/00* (2006.01)
(Continued)

(52) U.S. Cl.
CPC .............. *G06T 17/00* (2013.01); *A61B 6/025* (2013.01); *A61B 6/027* (2013.01); *A61B 6/466* (2013.01);
(Continued)

(58) Field of Classification Search
None
See application file for complete search history.

(56) References Cited

U.S. PATENT DOCUMENTS

2007/0232886 A1  10/2007 Camus et al.
2012/0148135 A1   6/2012 Van Rens et al.

FOREIGN PATENT DOCUMENTS

EP    2 049 021        4/2009
WO    2008/015612 A2   2/2008

OTHER PUBLICATIONS

Shengxian Tu et al., Assessment of obstruction length and optimal viewing angle from biplan X-ray angiograms, The International Journal of Cardiac Imaging, Kluwer Academic Publishers, DO vol. 26, No. 1, Sep. 18, 2009 pp. 5-17.
(Continued)

*Primary Examiner* — Frank S Chen
(74) *Attorney, Agent, or Firm* — Suiter Swantz pc llo

(57) ABSTRACT

The invention relates to method and apparatus for reconstructing a three-dimensional representation of a target volume inside an animal or human body.
Hereto, according to the method step ii) is preceded by the steps of:
a1) displaying said first two-dimensional image projection being obtained in step i) for a user using said displaying means,
(Continued)

a2) acquiring a first operational orientation setting of said imaging means corresponding with said first imaging position;
a3) defining based on said first operational orientation setting a first set of second operational orientation settings of said imaging means for orientation in a second imaging position;
a4) selecting from said set one of said second operational orientation settings;
a5) using said second operational orientation setting being selected for acquiring said second two-dimensional image projection of said target volume using said imaging means being positioned in the second imaging position corresponding to said second operational orientation setting.

Accordingly, with these features an improved reconstructing method is obtained, wherein an optimal set of two-dimensional image projections is obtained and proposed, based on which a correct three-dimensional contour image of said target volume is being reconstructed. Thus with this correct three-dimensional contour image the diagnostician is capable of performing a more accurate diagnosis and subsequent treatment of the patient, which in turn is subjected to a less lengthy imaging treatment session, which is beneficial in terms of radiation exposure time, discomfort, etc.

21 Claims, 9 Drawing Sheets

(51) Int. Cl.
*G06T 11/00* (2006.01)
*A61B 6/02* (2006.01)
(52) U.S. Cl.
CPC .............. *A61B 6/504* (2013.01); *A61B 6/508* (2013.01); *A61B 6/5205* (2013.01); *A61B 6/545* (2013.01); *G06T 11/003* (2013.01); *G06T 11/008* (2013.01); *A61B 6/486* (2013.01); *A61B 6/547* (2013.01)

(56) References Cited

OTHER PUBLICATIONS

Shengxian Tu et al., In vivo assessment of bifurcation optimal viewing angles and bifurcation angles by three-dimensional (3D) quantitative coronary angiography, The International Journal of Cardiac Imaging, Kluwer Academic Publishers, DO vol. 28, No. 7, Dec. 15, 2011, pp. 1617-1625.
International Search Report for International Application No. PCT/N12017/050310 dated Aug. 17, 2017.

METHOD AND APPARATUS FOR RECONSTRUCTING A THREE-DIMENSIONAL REPRESENTATION OF A TARGET VOLUME INSIDE AN ANIMAL OR HUMAN BODY

TECHNICAL FIELD AND BACKGROUND

The invention relates to method for reconstructing a three-dimensional representation of a target volume inside an animal or human body, said method comprising the steps of:

i) acquiring a first two-dimensional image projection of said target volume using imaging means being positioned in a first imaging position, ii) acquiring a second two-dimensional image projection of said target volume using said imaging means being positioned in a second imaging position, iii) reconstructing from said two-dimensional image projections a three-dimensional contour image of said target volume using transformation means, iv) displaying said three-dimensional contour image of said target volume fora user using displaying means.

The invention also relates to an apparatus for reconstructing a three-dimensional representation of a target volume inside an animal or human body, the apparatus comprising: an imaging means configured to obtain at least a first and a second two-dimensional image projection of a target volume within the animal or human body, each of said first and second two-dimensional image projection being obtained from a first and second imaging position of the imaging means respectively, wherein said first and second imaging position differ from each other; transformation means for reconstructing from said first and second two-dimensional image projections a three-dimensional contour image of said target volume; and displaying means for displaying said three-dimensional contour image of said target volume for a user.

It is common practice in the field of medicine to implement imaging techniques to view internal organs of a subject (patient). Said subject can be an animal or human body. When diagnosing for example the coronary blood circulation of said subject for coronary diagnosis an imaging means, for example an X-ray imaging device, is used to obtain image projections of the heart region and in particular of the blood vessels of the heart muscle (myocardium).

Herewith it is possible to identify any occlusion present in the coronary arteries and/or veins and to determine their location, size and extent of the occlusions if present.

Usually several two-dimensional image projections are needed and acquired from different view points (that is taken at different imaging positions of the imaging means relative to the patient) based on which a suitable three-dimensional contour image of the targeted organ is constructed. However the selection of the correct set of different two-dimensional image projections for the reconstruction of a three-dimensional representation (3D contour image) of the target volume still requires the acquisition and the analyzing by a diagnostician of multiple two-dimensional image projections before a decision on the correct set is being made.

This tends to lead to unnecessary lengthy imaging treatment session for the patient, which is undesirable due to radiation exposure, but also to incorrect selection of the correct set of image projections resulting in less accurate diagnosis and subsequent treatment of the patient.

BRIEF SUMMARY

It is an object of the invention to provide an improved method and apparatus for reconstructing a three-dimensional representation of a target volume inside an animal or human body allowing for a faster and more sophisticated imaging technique, thus reducing the acquisition and the analyzing time of the imaging diagnosis and limiting the imaging treatment session for the patient as well as avoiding diagnosis errors by the diagnostician.

Hereto, according to the method step ii) is preceded by the steps of:

a1) displaying said first two-dimensional image projection being obtained in step i) for a user using said displaying means, a2) acquiring a first operational orientation setting of said imaging means corresponding with said first imaging position;

a3) defining based on said first operational orientation setting a first set of second operational orientation settings of said imaging means for orientation in a second imaging position;

a4) selecting from said set one of said second operational orientation settings;

a5) using said second operational orientation setting being selected for acquiring said second two-dimensional image projection of said target volume using said imaging means being positioned in the second imaging position corresponding to said second operational orientation setting.

Accordingly, with these features an improved reconstructing method is obtained, wherein an optimal set of two-dimensional image projections is obtained and proposed, based on which a correct three-dimensional contour image of said target volume is being reconstructed. Thus with this correct three-dimensional contour image the diagnostician is capable of performing a more accurate diagnosis and subsequent treatment of the patient, which in turn is subjected to a less lengthy imaging treatment session, which is beneficial in terms of radiation exposure time, discomfort, etc.

In a further aspect of the method, method step a3) comprises the step of a3a defining a first subset of second operational orientation settings of said imaging means for orientation in said second imaging position, said first subset of second operational orientation settings being distinct from said first operational orientation setting.

By defining a first subset of second operational orientation settings of said imaging means for orientation in said second imaging position, wherein said first subset of second operational orientation settings is distinct from said first operational orientation setting any duplication of acquiring identical or more or less identical two-dimensional image projections is being avoided. Herewith the length if the imaging treatment session is further reduced (which is beneficial for the patient), but also incorrect or unsuitable three-dimensional contour images are not reconstructed thus avoiding incorrect analysis and diagnosis of the target volume of the patient by the diagnostician.

More in particular method step a3) comprises the step of a3b defining a second subset of second operational orientation settings of said imaging means for orientation in said second imaging position, said second subset of second operational orientation settings being conformal to said first operational orientation setting.

This second subset defines and represents a series of operational orientation settings which are conformal to the operational orientation setting belonging to the first image projection being acquired and thus should be avoided when acquiring a second image projection of the target volume. With this 'no-go set' operational orientation settings analysis and diagnosis errors of the target volume of the patient by the diagnostician are avoided.

In particular as the method step a4) comprises the step of selecting said one of said second operational orientation settings from said first subset of second operational orientation settings an improved reconstructing method is obtained resulting in a correct three-dimensional contour image based on which the diagnostician is capable of performing a more accurate diagnosis and subsequent treatment of the patient.

In further aspect method step a4) is preceded by the step of determining a longitudinal orientation of said target volume in said first two-dimensional image projection. In particular method step a4) comprises the step of selecting said one of said second operational orientation settings to correspond to a second imaging position being defined in a plane perpendicular to said longitudinal orientation of said target volume being determined.

Herewith two distinct image projections are acquired based on which a correct three-dimensional contour image is being reconstructed and thus a correct analysis and diagnosis of the target volume of the patient by the diagnostician can be performed.

The acquisition of two distinct image projections and the resulting three-dimensional contour image is thus obtained as the step of determining said longitudinal orientation of said target volume in said first two-dimensional image projection comprises the steps of defining in said first two-dimensional image projection a first point of interest inside said target volume as well as a second point of interest inside said target volume and determining said longitudinal orientation of said target volume based on said first and second point of interest.

In particular said first subset of second operational orientation settings limit an angle between a first plane in which said first imaging position corresponding to said first operational orientation setting is defined and a second plane in which said second imaging positions corresponding to said second operational orientation settings are defined between a range of 35°-50°. Herewith the acquisition of an incorrect set of two-dimensional image projections and an inaccurate three-dimensional contour image based on this set is thus avoided further improving the reconstructing method according to the invention.

In a further automation of the reconstruction method of the invention the method step a5) is preceded by the step of positioning said imaging means in said second imaging position corresponding to said second operational orientation setting.

In particular said target volume is a coronary artery and said imaging means comprise an X-ray imaging device.

In the apparatus for reconstructing a three-dimensional representation of a target volume inside an animal or human body according to the invention said displaying means are arranged for displaying said first two-dimensional contour image of the target volume being obtained with the imaging means being positioned in said first imaging position for a user; and said transformation means are arranged for acquiring a first operational orientation setting of said imaging means corresponding with said first imaging position; and for defining based on said first operational orientation setting a first set of second operational orientation settings of said imaging means for orientation in a second imaging position; and for selecting from said first set one of said second operational orientation settings; and for using said second operational orientation setting being selected for acquiring said second two-dimensional image projection of said target volume using said imaging means being positioned in the second imaging position corresponding to said second operational orientation setting.

Accordingly, with these features an improved apparatus for reconstructing a three-dimensional representation of a target volume is obtained, wherein an optimal set of two-dimensional image projections is obtained and proposed, based on which a correct three-dimensional contour image of said target volume is being reconstructed. Thus with this correct three-dimensional contour image the diagnostician is capable of performing a more accurate diagnosis and subsequent treatment of the patient, which in turn is subjected to a less lengthy imaging treatment session, which is beneficial in terms of radiation exposure time, discomfort, etc.

BRIEF DESCRIPTION OF THE DRAWINGS

The invention will now be described in more detail with reference to the accompanying drawings, which drawings show in:

FIGS. 4-8B show details of the implementation of the method according to the invention.

DETAILED DESCRIPTION

Figure 1:
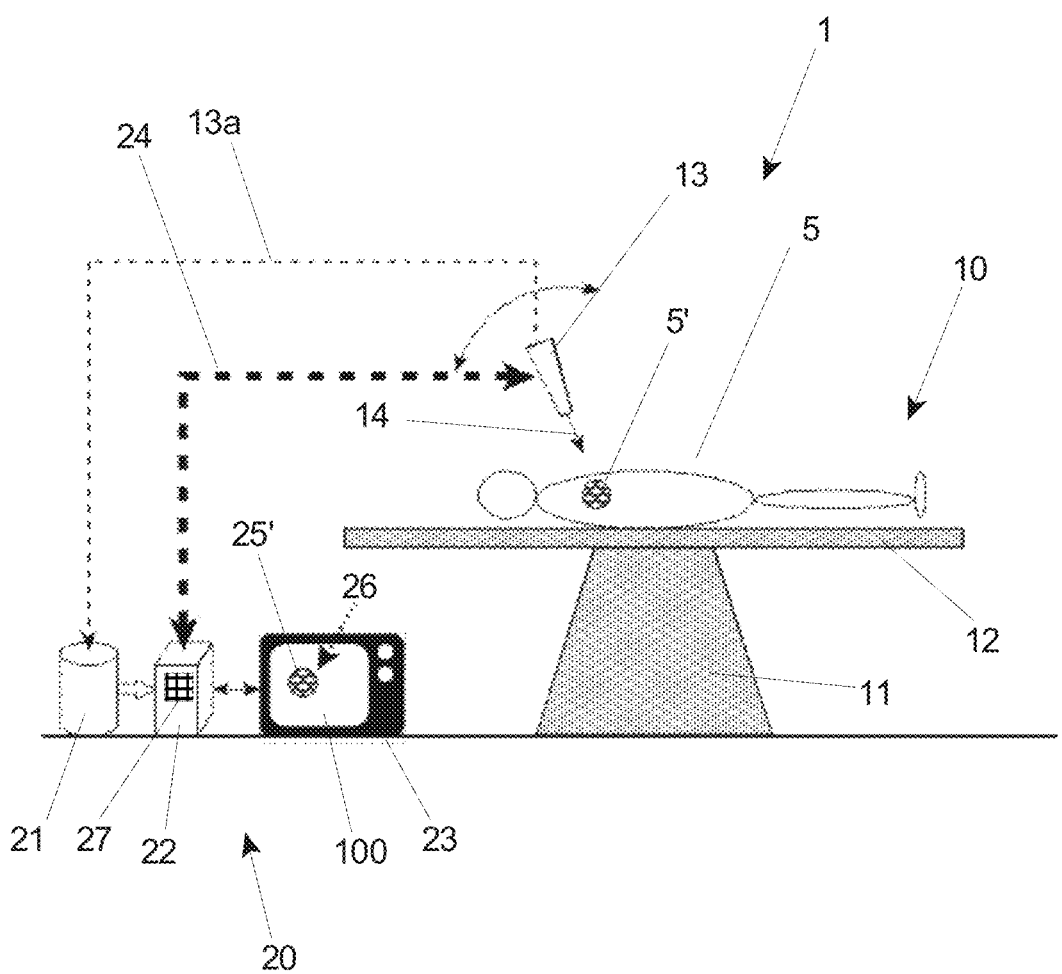
FIG. 1 shows in very schematic form an imaging device implementing the method and an apparatus according to the invention.

FIG. 1 shows in very schematic form various elements of a known imaging device 10. An object 5, here a human patient 5 is shown lying in lithotomy position on a table 12 which is supported by a base 11. Above the table 12 imaging means 13 are positioned which imaging means 13 are movable accommodated in a structure (not shown) forming part of the imaging device 10. This allows for a controlled positioning of the imaging means 13 at any angle or orientation relative to a target volume 5' inside the patient's body 5.

The imaging means 13 can be any imaging technique capable of obtaining 2D image projection of a target volume (here indicate with reference numeral 5) in an object 5. For example X-ray radiation imaging means can be used when implementing the method and apparatus according to the invention.

It should be noted that the object 5 lying on the table 12 can be a human or animal body or any other object which is to be subjected to the apparatus and method according to the invention.

According to the invention the imaging device 10 during operation interact with a data acquisition apparatus 20. Data acquisition apparatus 20 can be a separate apparatus that is communicatively linked to the imaging device 10 or the data acquisition apparatus 20 can form an integral part of the imaging device 10. Data acquisition apparatus 20 is at least composed of a data image storage 21, a processing unit 22 and a display unit 23. The data storage unit 21 is communicatively connected with the imaging means 13 via data-communication link 13a. Data storage unit 21 is bi-directionally connected to the processing unit 22, which in turn is bi-directionally connected to the display unit/means 23. Also processing unit 22 is bi-directionally connected to the imaging device 13 via communication link 24.

Preferably the storage unit 21, the processing unit 22 and the display unit/means 23 are constructed in one constructional entity, however they can also be separate parts.

The processing unit 22 or the display unit 23 also comprises image transformation means 27 (in FIG. 1 depicted as being comprises in the processing unit 22) for reconstructing a three-dimensional contour image of the target volume from (using) two-dimensional image projections being acquired with the imaging means 13.

Figure 2A:
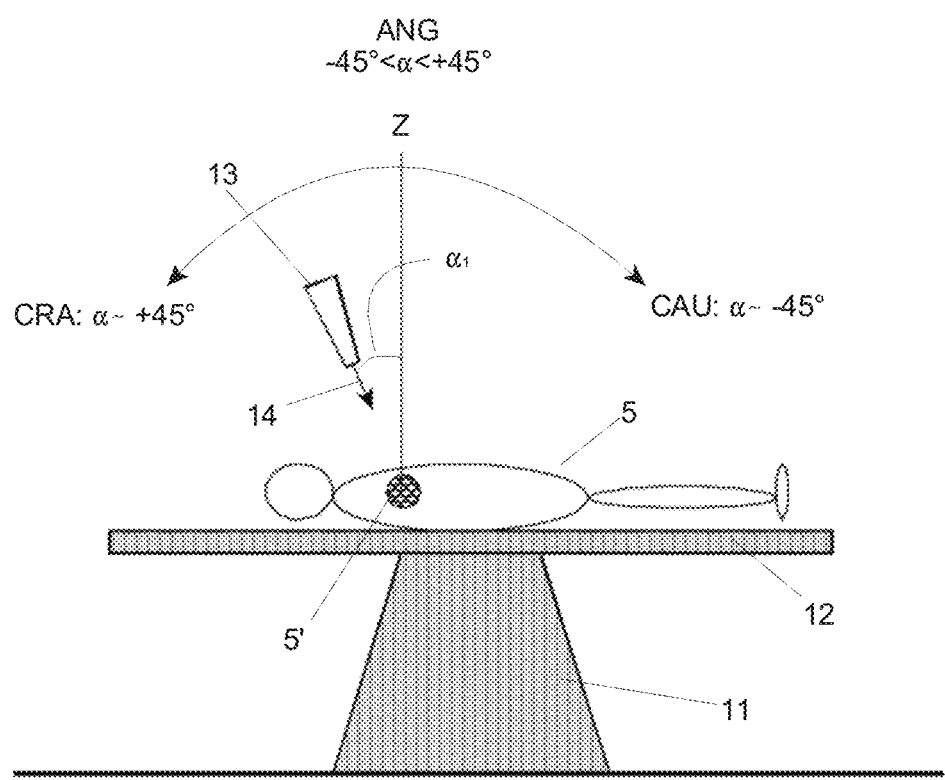
FIGS. 2a-2b show two side views of FIG. 1.
Figure 2B:
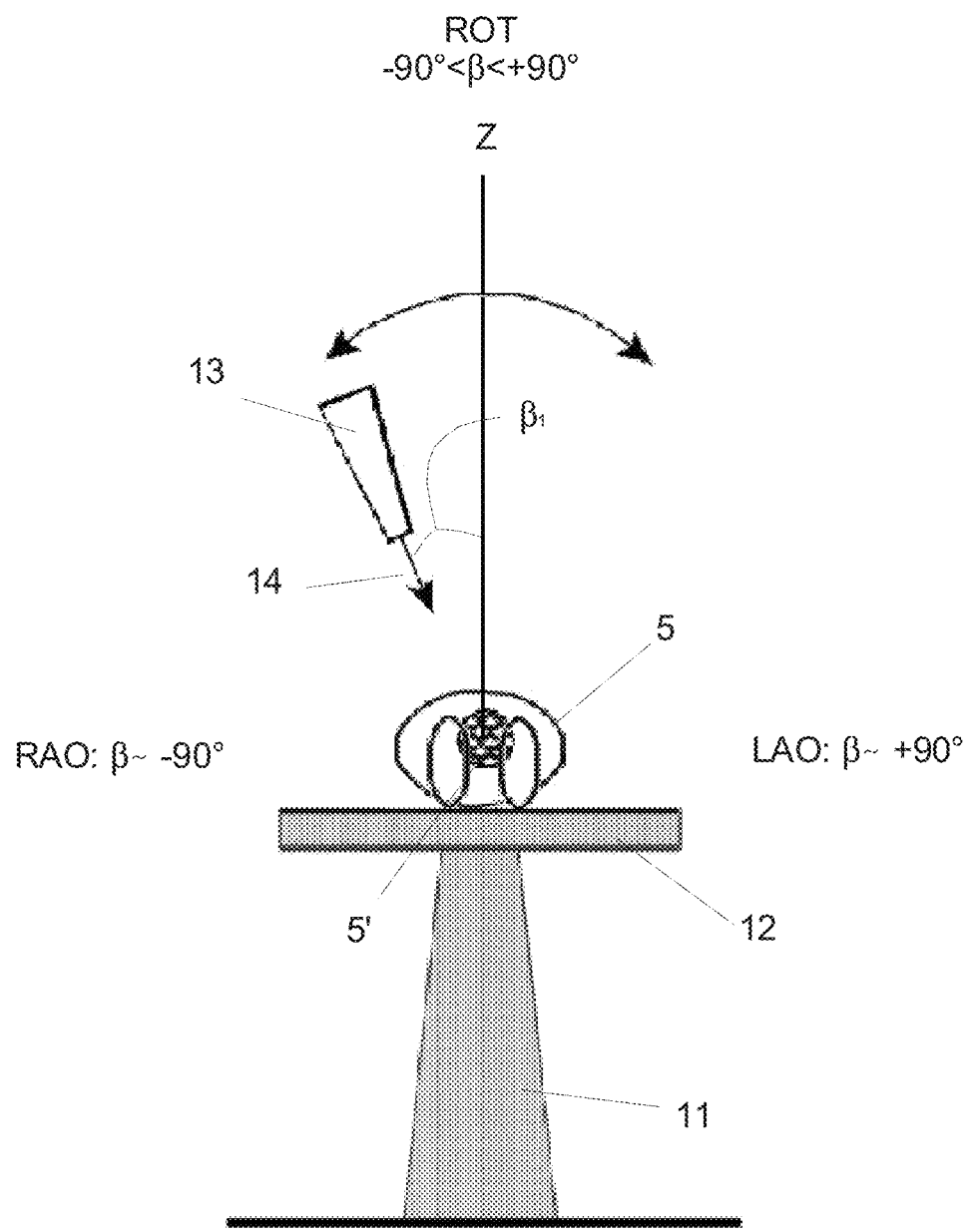

In FIGS. 2A and 2B two side views are shown of the apparatus as shown in FIG. 1. In FIG. 2A the apparatus according to the invention is shown with the patient 5 lying in longitudinal direction. The imaging device 13 as shown in this side view of FIG. 2A is positioned at an angle $\alpha 1$ relative to a vertical axis Z which is orientated perpendicular to the horizontal table 12 on which the patient 5 is positioned. Also, the vertical axis Z points directly to the target volume 5' which in this example represents the heart of the patient 5. As shown in FIG. 2A, imaging device 13 is positioned at an angle $\alpha 1$ relative to the vertical axis Z pointing towards the target volume 5'.

During operation the imaging device 13 will emit X-ray radiation 14 towards the target volume 5' to acquire a two-$\alpha$dimensional image projection of the target volume 5'. These imaging techniques are known in the art.

As clearly shown in FIG. 2A, the imaging device 13 can be orientated in a range of angles, where positive angles are denoted CRA (Cranial) and negative angles are denoted CAU (Caudal) relative to the body of the patient, which angle ANG ranges between the extreme angle CRA45 ($\alpha = +45°$) near the head of the patient and the other extreme angle CAU45 ($\alpha = -45°$) near the feet/extreme end of the patient). At $\alpha = 0°$, the imaging device 13 is positioned right above the patient 5 at the axis Z. In FIG. 2A the imaging device 13 is shown as being positioned approximately at the position CRA 15, meaning $\alpha = 15°$.

In FIG. 2B a frontal view is shown which corresponds with the side view as depicted in FIG. 2A. In FIG. 2B it is shown that the imaging device 13 can also be positioned at different angles ROT in the range of $\beta \approx -90°$ (the right anterior oblique view RAO) and $\beta \approx +90°$ (left anterior oblique view LAO).

Each two-dimensional image projection obtained with the imaging device 13 can be characterised by its angular orientation relative to the patient 5 by means of its angular orientation $\alpha$ (ANG) and rotational orientation $\beta$ (ROT) relative to the object 5 lying on the table 12.

Figure 3:
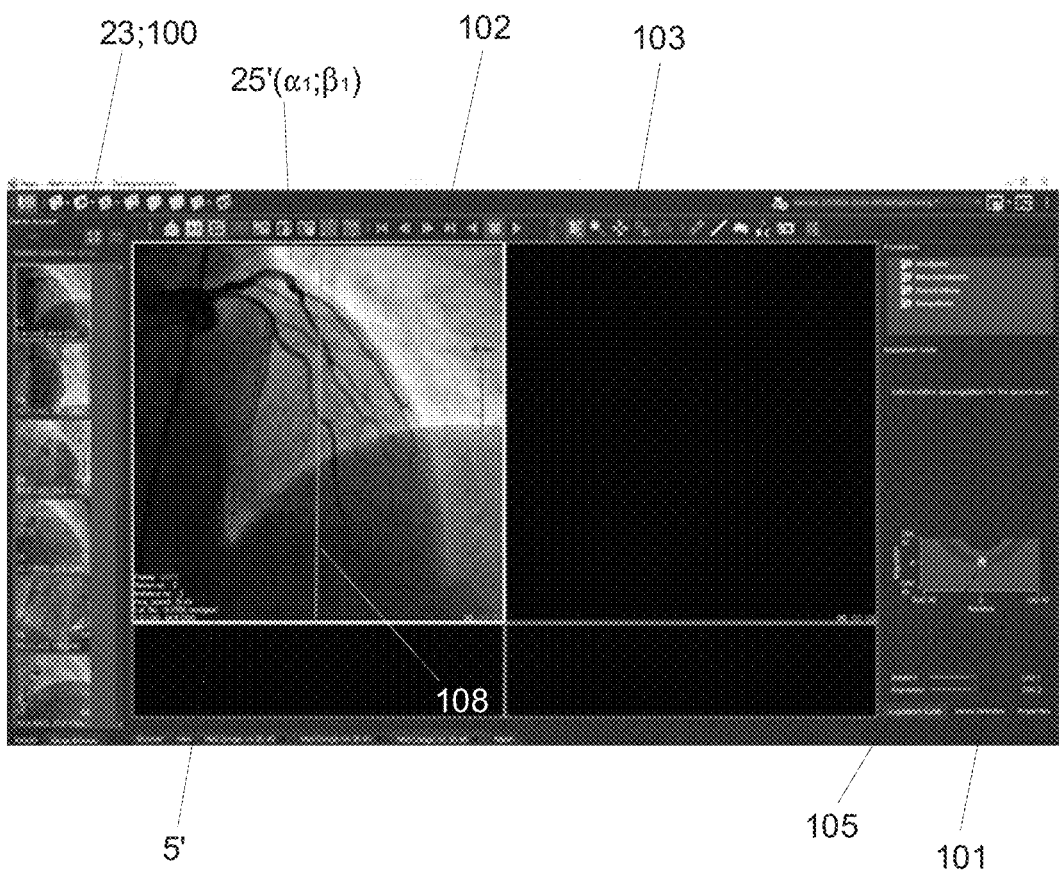
FIG. 3 shows a first implementation of the method according to the invention.

Such a two-dimensional image projection is for example shown in FIG. 3. FIG. 3 depicts an implementation of the method according to the invention as implemented in an apparatus 23 according to the invention. Reference numeral 23 corresponds to the display unit 23 as shown in FIG. 1 and implements a working environment on a display means. A part of the working environment 100 (working environment field 102) is used to display the first image projection 25' that depicts the target volume 5' in a two-dimensional projection. It is noted that the two-dimensional image projection 25' as shown in the working environment 102 has been obtained with the imaging device 13 being positioned in an angular orientation $\alpha 1$ and a rotational orientation $\beta 1$.

The method and apparatus according to the invention implements transformation means 27 for reconstructing a three-dimensional contour image of the target volume 5' from (using) at least two different two-dimensional image projections being obtained with the imaging device 13 for analysis and diagnosis by an user or diagnostician. At least two different two-dimensional image projections are to be acquired using the imaging device 13, which two two-dimensional image projections need to be sufficiently distinct from each other in order to acquire an accurate 3D representation after reconstruction.

It will be clear that if the two image projections being used are both obtained at more or less the same orientation (position) of the imaging device 13 relative to the target volume 5, both image projections more or less will overlap in the same two-dimensional plane of the projections and an accurate 3D reconstruction is less feasible or even impossible.

Hereto, according to the method and apparatus according to the invention, the first two-dimensional image projection obtained at the angular orientation $\alpha 1$ and the rotational orientation $\beta 1$ of the imaging device 13 is acquired via the imaging device 13 and stored in the storage unit 21 via the communication link 13a. The processing unit 22 acquires the first two-dimensional image projection from the storage unit 21 and communicates it towards the display unit 23.

The display unit 23 displays the first two-dimensional image projection 25' (characterised by the angular orientation $\alpha 1$ and the rotational orientation $\beta 1$ corresponding with the first imaging position) is displayed at the working environment field 102 of the working environment 100 of the display means. Simultaneously, the first operational orientation setting ($\alpha 1$; $\beta 1$) which represents the angular and rotational orientation of the imaging device 13 at the time of acquiring the first two-dimensional image projection 25' is acquired by the processing unit 22 and/or the display unit 23.

Based on the first operational orientation setting ($\alpha 1$; $\beta 1$) a first set of second operational orientation settings ($\alpha 2$; $\beta 2$) is defined. The first set of second operational orientation settings ($\alpha 2$; $\beta 2$) represents a set of possible second imaging positions characterised by angular orientation $\alpha 2$ and rotational orientation $\beta 2$ in which the imaging device 13 can be positioned for acquiring a second image projection 25" which can be used together with the first orientation projection 25' acquired in the first imaging position ($\alpha 1$; $\beta 1$) for reconstructing a three-dimensional representation of the target volume. 5'

Said first set of second operational orientation settings ($\alpha 2$; $\beta 2$) is being calculated and represented in the operational work field 101 of FIG. 3 and in more detail in FIG. 4.

The first set of second operational orientation settings ($\alpha 2$; $\beta 2$) is represented with reference numeral 112 in FIG. 4. Said first set 112 represents all possible orientations of the imaging device 13 in terms of an angular orientation $\alpha 2$ and a rotational orientation $\beta 2$ relative to the target volume 5' as shown in FIGS. 2A and 2B. The angular orientation $\alpha 2$ can be set between CAU 45 and CRA 45 represented by $-45°$ respectively $+45°$. The rotational orientation $\beta 2$ can be set between the right anterior oblique view and left anterior oblique view represented by $-90°$ respectively $+90°$.

In particular, according to a further aspect of the method according to the invention, the first set 112 of possible second operational orientation settings ($\alpha 2$; $\beta 2$) is being defined in a first subset 113 and a second subset 114 of second operational orientation settings. The first subset of second operational settings 113 represents an optimum subset of second operational orientation settings ($\alpha 2$; $\beta 2$) which are clearly distinct from the first operational orientation setting ($\alpha 1$; $\beta 1$).

Likewise, the second subset of second operational orientation settings 114 represent a subset of second operational orientation settings which are more or less conformal to the first operational orientation setting ($\alpha 1$; $\beta 1$). The method and the apparatus according to the invention determines and displays both the first subset 113 and the second subset 114 of second operational orientation settings of the imaging device 13.

The method and the apparatus operate such that it is decided to rule out the second subset 114 of second operational orientation settings as possible choices for a second imaging position for the imaging device 13. In particular the method and apparatus according to the invention defines the first subset 113 of second operational orientation settings (α2; β2) as the preferred subset from which one specific distinct second operational orientation setting (α2; β2) is being selected.

The preferred first subset 113 of second operational orientation settings (α2; β2) limit an angle between a first plane in which said first imaging position corresponding to said first operational orientation setting is defined and a second plane in which said second imaging positions corresponding to said second operational orientation settings are defined between a range of 35°-50°. This is shown in the operational work field 101 as a wide curved band.

Figure 4:
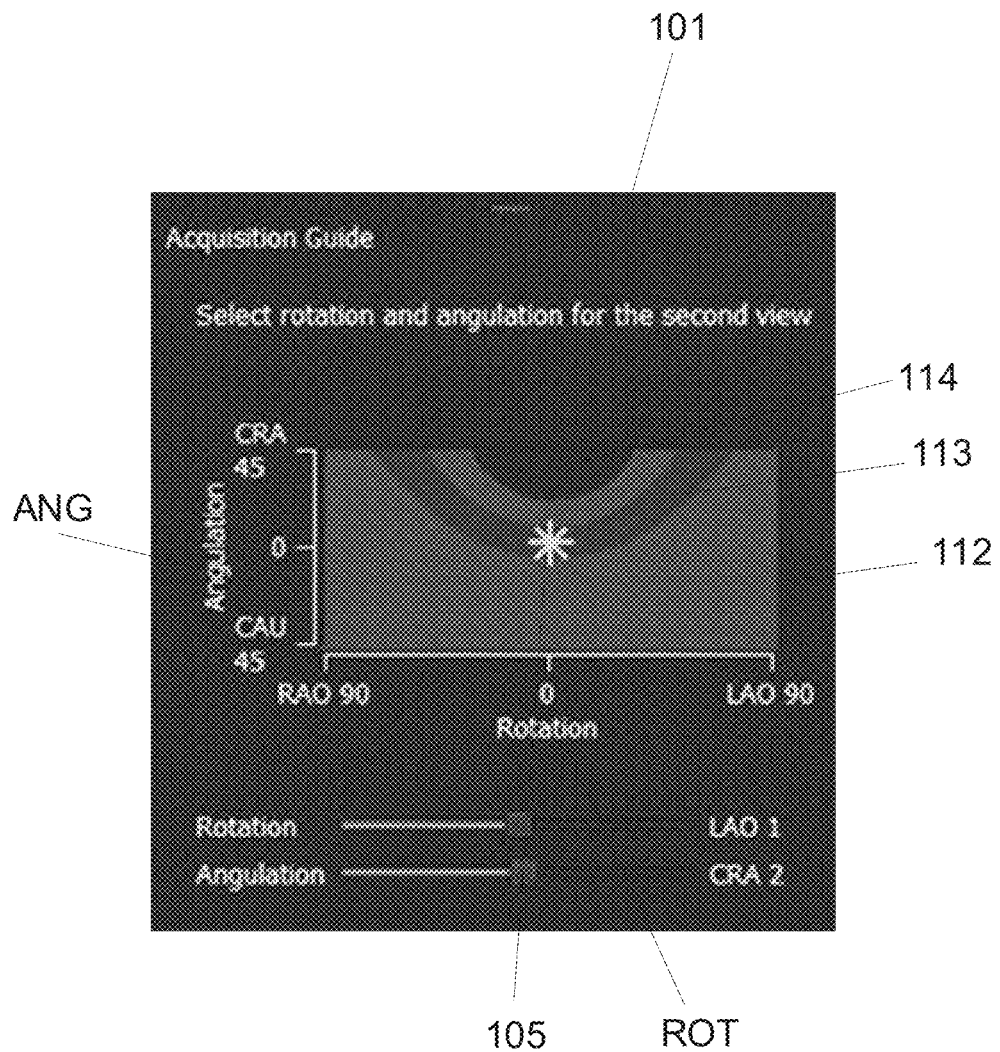

In FIGS. 3 and 4 the white star indicated with reference numeral 105 represents the orientation of the imaging means 13 in its second imaging position here represented with ANG orientation α2=2° and ROT orientation β2=1° (CRA 2 and LAO 1, see FIG. 4). This means that in the second imaging position the imaging device 13 would be located approximately at the axis Z (see FIGS. 1, 2a and 2b) above the patient 5 and the target volume 5'.

This second imaging position is a suggested imaging position and is depicted in an imaginary manner in the first image projection 25' (α1; β1) as displayed in work environment field 102 as the oblique white line 108. This line 108 defines a plane across the target volume 5' in which the imaging device 13 is positioned relative to the patient's body. The white line 108 provides a first indication whether the second image projection 25" (α2; β2) being taken in said proposed second imaging position is sufficiently suitable in combination with the first image projection 25' such that after transformation of both image projections the three-dimensional target volume thus reconstructed is usable for analysis and diagnosis purposes.

Figure 5:
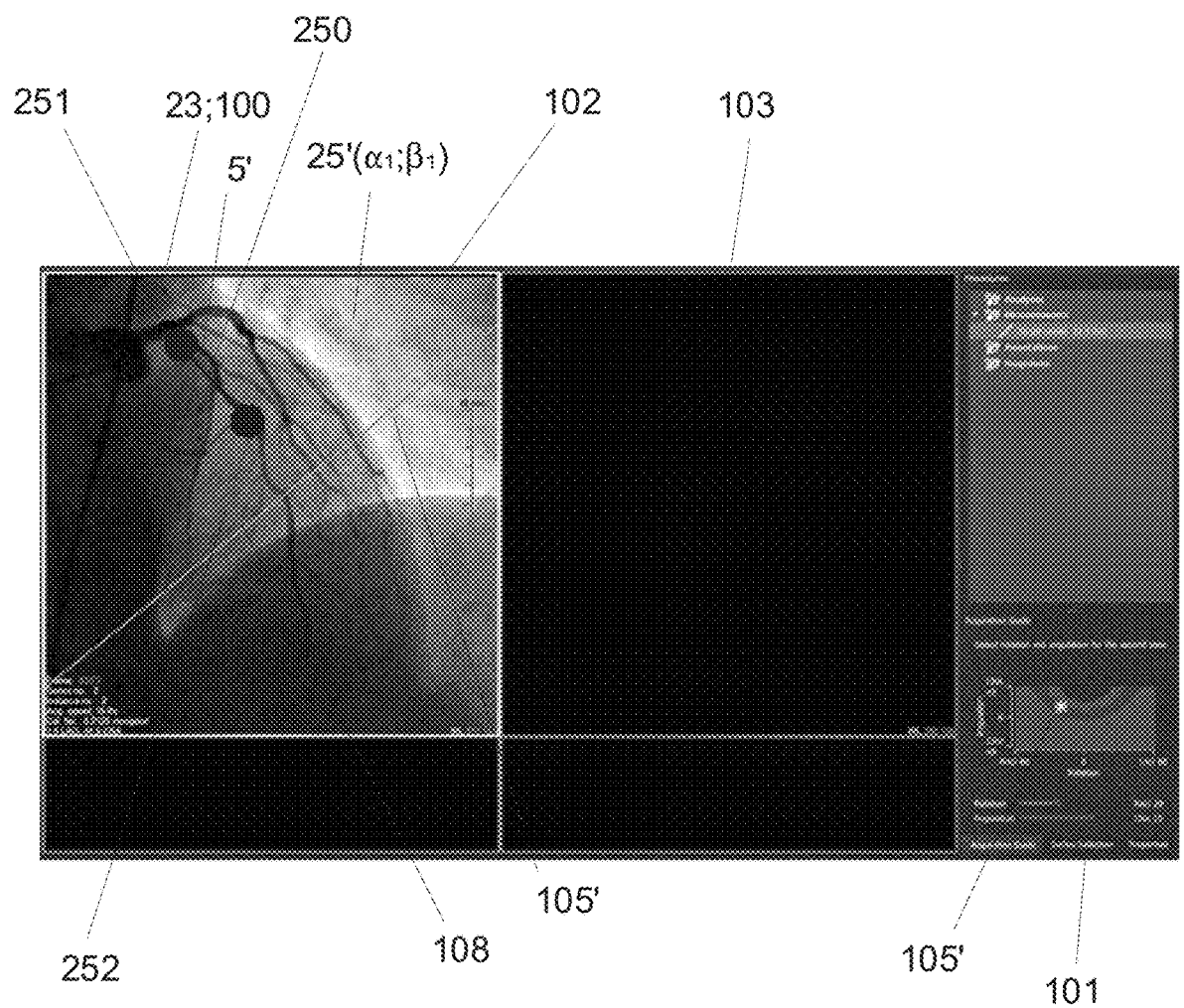
Figure 6:
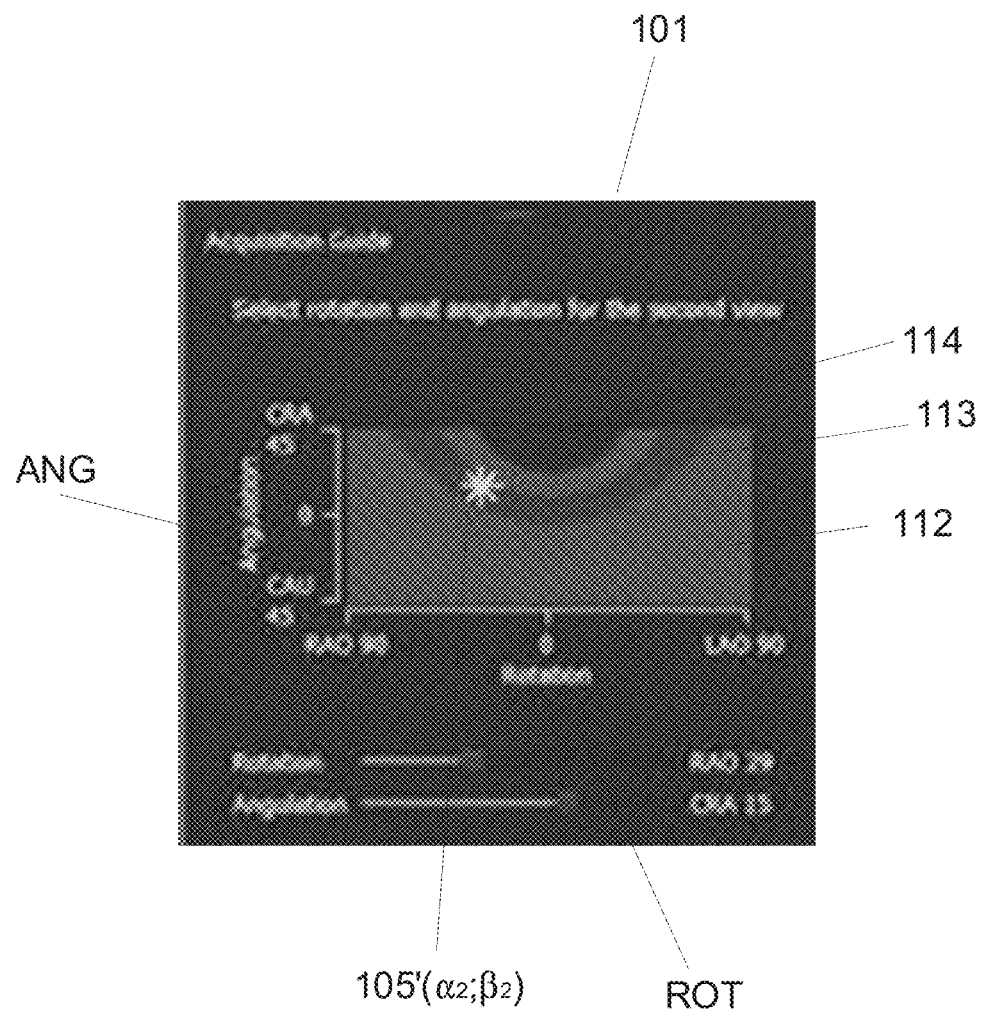

The method and apparatus according to the invention are capable of selecting the second operational orientation setting from the first subset 113 such that said second operational orientation setting corresponds to a second imaging position of the imaging means 13, which second imaging position is clearly distinct from the first imaging position. The second operational orientation setting being selected from the first subset 113 is depicted in FIG. 5 in the work environment field 101 as a white star which is shifted within the first subset 113 compared to the orientation of the white star 105 as shown in FIG. 4. In FIG. 5 and in particular in the work environment field 101 the white star is indicated with the reference numeral 105' (α2; β2).

Figure 7:
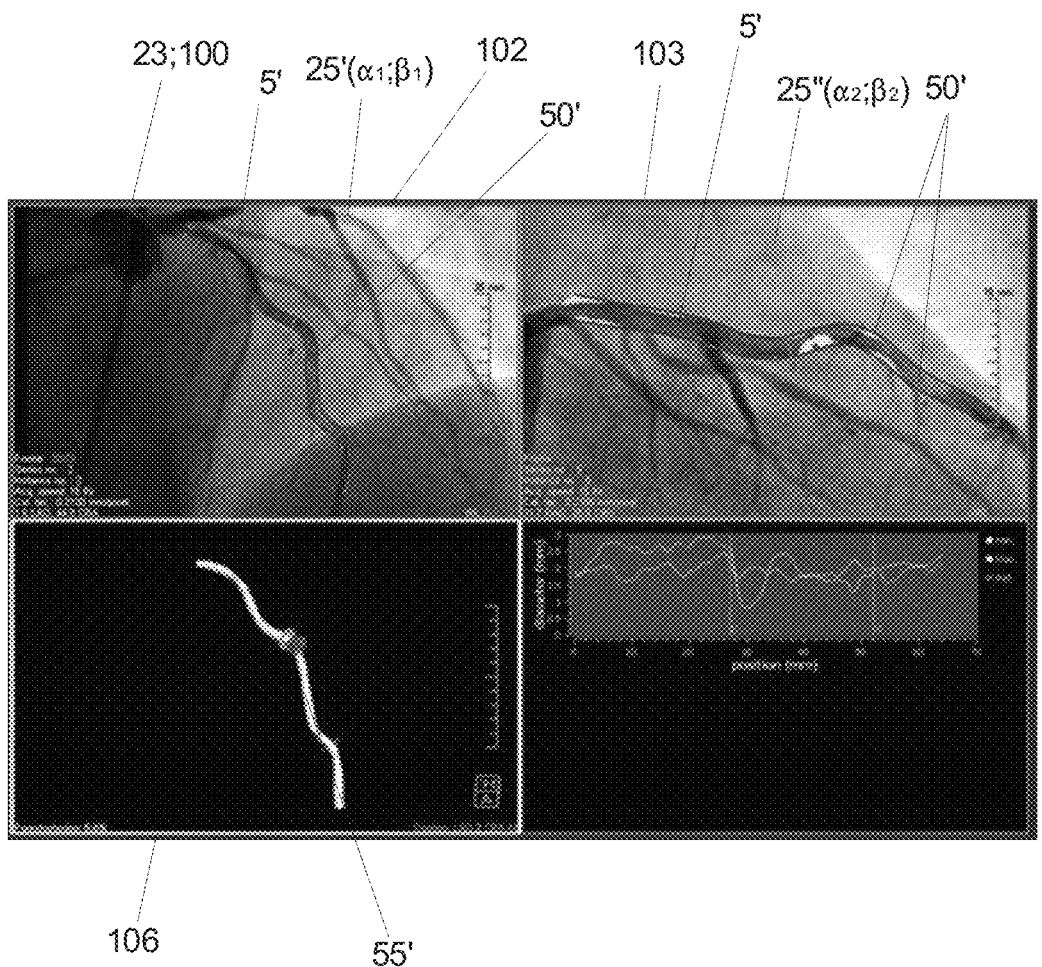

The second image projection being acquired with the imaging means 13 positioned in the second imaging position corresponding with the second operational orientation setting 105' (α2; β2) is stored in the storage unit 21 via the data communication link 13a and processed by the processing unit 22 towards the display unit 23 for display in the work environment field 103 as depicted in FIG. 7. Both the first and the second image projections 25' (α1; β1) and 25" (α2; β2) are depicted next to each other for the user and the transformation means 27 process both image projections 25' and 25" in order to acquire the outer contours 50' of the target volume 5'.

In this example the target volume 5' is an artery of the coronary artery system.

Figure 8:
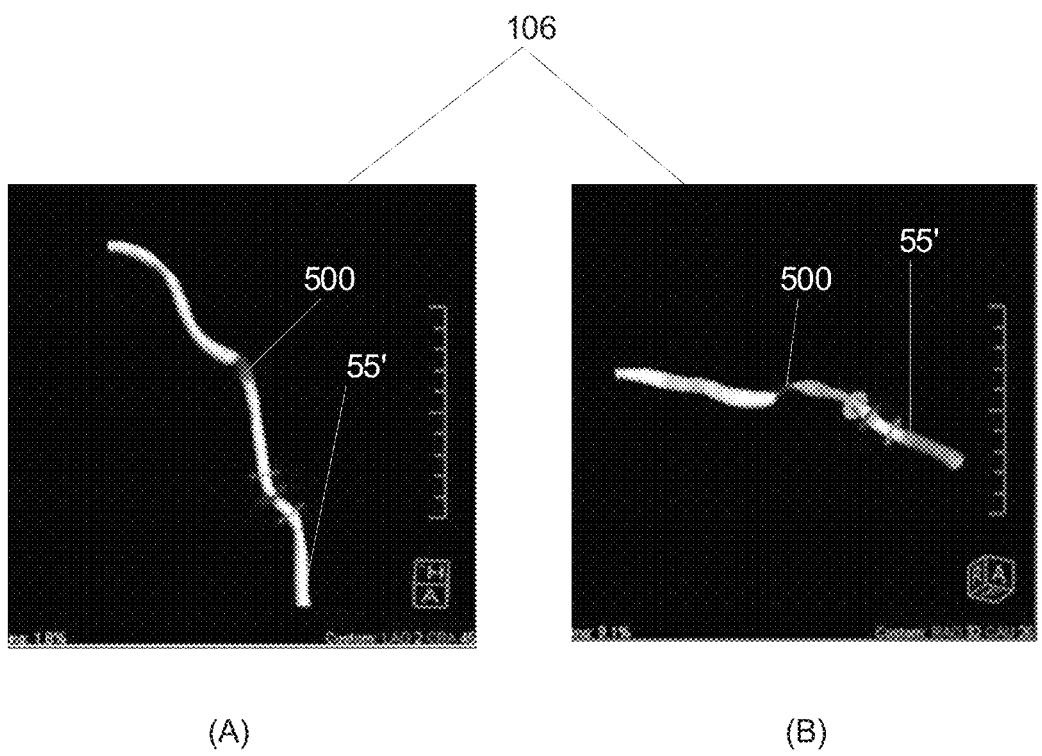

The transformation means process both images 25' and 25" for reconstructing a three-dimensional contour image of the target volume 5' which is displayed in work environment field 106 in FIG. 7 and FIGS. 8a and 8b. By manipulating the reconstructed three-dimensional contour image of the target volume 5', here an artery, the user or diagnostician is allowed to view the target volume 5' (artery 5') from all sides in order to observe any ailments or affects such as an occlusion 500 in the artery.

Thus with the method and apparatus according to the invention it is obviated that two more or less identical (or better less distinct) image projections are acquired and transformed for reconstructing a far less accurate three-dimensional contour image. With such less accurate three-dimensional contour image an incorrect or incomplete analysis and diagnosis would be performed as certain ailments would be become visible in the inaccurate three-dimensional contour image even when the three-dimensional contour image is manipulated and rotated on the display means by the user.

As a further support for selecting the correct second operational orientation setting 105' the method and apparatus according to the invention are arranged in determining a longitudinal orientation of the target volume 5' in said first two-dimensional image projection 25' as depicted in work environment field 102 of the display unit 23.

The determination and display of the longitudinal orientation of the target volume 5' is represented with reference numeral 250 in FIG. 5. In particular in this embodiment the target volume 5' represents an artery of the coronary artery system to be examined. In order to properly define and determine the longitudinal orientation of said artery 5' the method and the apparatus are arranged in defining in said first image projection 25' a first point of interest 251 and a second point of interest 252. Both said first and second points of interest are inside the target volume 5' to be examined.

The method and apparatus according to the invention, in particular the display unit 23, are arranged in determining said longitudinal orientation 250 of the target volume 5' by interconnecting said first and second point of interest 251 and 252 respectively.

The method and apparatus according to the invention are assisted in selecting the optimal second operational orientation setting 105' by using the longitudinal orientation 250 being determined inside the first image projection 25' of the target volume 5' to be examined. In particular the second operational orientation setting 105' is selected from the first subset 113 under the additional condition that the second imaging position corresponding to said second operational orientation setting 105' being selected, is being defined in a plane perpendicular or nearly perpendicular to the longitudinal orientation 250 as determined in the target volume 5' under examination.

This additional perpendicular condition is depicted in FIG. 5 in the work environment field 102 as the oblique white line 108 defines a plane perpendicular to the longitudinal orientation 250 as defined across the target volume 5' (being the longitudinal orientation of the artery under examination). The second operational orientation setting 105' as being selected from the first subset 113 corresponds to the second imaging position of the imaging means 13.

As such it can be assured by the method and apparatus according to the invention that the first and second imaging position of the imaging means 13 are sufficiently distinct from each other and that therefore no overlapping two-dimensional image projections 25' and 25" are acquired which would render the reconstructed three-dimensional contour image of the target volume 5' as unusable for a proper examination and diagnosis by a user (physician or diagnostician).

In addition, the user can input additional instructions using a pointing or inputting device such as a computer mouse to the display unit 23 by selecting and relocating the white star within the work environment field 101 and in particular within the set 112 of possible second operational orientation setting (within the first and/or second subset 113 and 114). Based on said input the apparatus and method according to the invention will provide immediate feedback to the user as to the possible orientation 105' of the imaging means 13 relative to the target volume 5'.

As such it can be decided whether said manually relocated second imaging position 105' can be used in real time for acquiring the second image projection to be displayed in work environment field 103. The manual operation of the display unit/means 23 by the user is in FIG. 1 depicted with the reference numeral 26.

With the method and apparatus according to the invention the diagnostician is capable of performing a more accurate diagnosis and subsequent treatment of the patient as the correct second imaging position of the imaging means 13 can be determined in advance thereby reducing the imaging treatment session for the patient which is beneficial in terms of reduced radiation exposure time, limited discomfort, etc.

Apart from the length of the image treatment session being reduced also incorrect or unsuitable (meaning overlapping or less distinct) two-dimensional image projections are not acquired and as such an unsuitable three-dimensional contour image is not reconstructed. Also herewith an incorrect analysis and diagnosis of the target volume of the patient by the user is avoided.

A fully automated operation of the imaging means 13 is also disclosed in FIG. 1 wherein the processing unit 22 is connected with the imaging means 13 via a bidirectional data communication link 24. Via said bidirectional data communication link 24 the processing unit 22 not only acquires or reads out the first operational orientation setting ($\alpha 1; \beta 1$) from the imaging device 13 when acquiring the first two-dimensional image projection in the first imaging position. The processing unit 22 is also arranged in programming or setting the imaging device 13 with the selected second operational orientation setting ($\alpha 2; \beta 2$) based on which the imaging device 13 is properly positioned in the second imaging position at the angular orientation $\alpha 2$ and rotational orientation $\beta 2$ thus selected by the method and apparatus according to the invention for acquiring the second two-dimensional image projection.

The invention claimed is:

1. A method for reconstructing a three-dimensional representation of a target volume inside an animal or human body, said method comprising the steps of:
    i) acquiring a first two-dimensional image projection of said target volume using imaging means being positioned in a first imaging position,
    ii) acquiring a second two-dimensional image projection of said target volume using said imaging means being positioned in a second imaging position,
    iii) reconstructing from said two-dimensional image projections a three-dimensional contour image of said target volume using transformation means,
    iv) displaying said three-dimensional contour image of said target volume for a user using displaying means, wherein step ii) is preceded by the steps of:
        a1) displaying said first two-dimensional image projection being obtained in step i) for a user using said displaying means,
        a2) acquiring a first operational orientation setting of said imaging means representing an operational orientation setting corresponding with said first imaging position of said imaging means at a time of acquiring said first two-dimensional image projection;
        a3) defining based on said first operational orientation setting a first set of second operational orientation settings of said imaging means for orientation in a second imaging position;
        a4) selecting from said set one of said second operational orientation settings;
        a5) using said second operational orientation setting being selected for acquiring said second two-dimensional image projection of said target volume using said imaging means being positioned in the second imaging position corresponding to said second operational orientation setting.

2. The method according to claim 1, wherein step a3) comprises the step of
    a3a) defining a first subset of second operational orientation settings of said imaging means for orientation in said second imaging position, said first subset of second operational orientation settings being distinct from said first operational orientation setting.

3. The method according to claim 2, wherein step a4) comprises the step of selecting said one of said second operational orientation settings from said first subset of second operational orientation settings.

4. The method according to claim 2, wherein said first subset of second operational orientation settings limit an angle between a first plane in which said first imaging position corresponding to said first operational orientation setting is defined and a second plane in which said second imaging positions corresponding to said second operational orientation settings are defined between a range of 35°-50°.

5. The method according to claim 1, wherein step a3) comprises the step of
    a3b) defining a second subset of second operational orientation settings of said imaging means for orientation in said second imaging position, said second subset of second operational orientation settings being conformal to said first operational orientation setting.

6. The method according to claim 1, wherein step a4) is preceded by the step of determining a longitudinal orientation of said target volume in said first two-dimensional image projection.

7. The method according to claim 6, wherein step a4) comprises the step of selecting said one of said second operational orientation settings to correspond to a second imaging position being defined in a plane perpendicular to said longitudinal orientation of said target volume being determined.

8. The method according to claim 6, wherein the step of determining said longitudinal orientation of said target volume in said first two-dimensional image projection comprises the steps of defining in said first two-dimensional image projection a first point of interest inside said target volume as well as a second point of interest inside said target volume and determining said longitudinal orientation of said target volume based on said first and second point of interest.

9. The method according to claim 1, wherein step a5) is preceded by the step of positioning said imaging means in said second imaging position corresponding to said second operational orientation setting.

10. The method according to claim 1, wherein said target volume is a blood vessel of the heart muscle.

11. The method according to claim 1, wherein said imaging means comprise an X-ray imaging device.

12. An apparatus for reconstructing a three-dimensional representation of a target volume inside an animal or human body, the apparatus comprising:
- an imaging means configured to obtain at least a first and a second two-dimensional image projection of a target volume within the animal or human body, each of said first and second two-dimensional image projection being obtained from a first and second imaging position of the imaging means respectively, wherein said first and second imaging position differ from each other;
- transformation means for reconstructing from said first and second two-dimensional image projections a three-dimensional contour image of said target volume;
- displaying means for displaying said three-dimensional contour image of said target volume for a user; wherein said displaying means are arranged for displaying said first two-dimensional contour image of the target volume being obtained with the imaging means being positioned in said first imaging position for a user; and wherein said transformation means are arranged for acquiring a first operational orientation setting of said imaging means representing an operational orientation setting corresponding with said first imaging position of said imaging means at a time of acquiring said first two-dimensional image projection; and
- for defining based on said first operational orientation setting a first set of second operational orientation settings of said imaging means for orientation in a second imaging position; and
- for selecting from said set one of said second operational orientation settings; and
- for using said second operational orientation setting being selected for acquiring said second two-dimensional image projection of said target volume using said imaging means being positioned in the second imaging position corresponding to said second operational orientation setting.

13. The apparatus according to claim 12, wherein the transformation means are further arranged for defining a first subset of second operational orientation settings of said imaging means for orientation in said second imaging position, said first subset of second operational orientation settings being distinct from said first operational orientation setting.

14. The apparatus according to claim 13, wherein the transformation means are arranged for selecting said one of said second operational orientation settings from said first subset of second operational orientation settings.

15. The apparatus according to claim 13, wherein the transformation means are arranged in defining said first subset of second operational orientation settings such, that said first subset limit an angle between a first plane in which said first imaging position corresponding to said first operational orientation setting is defined and a second plane in which said second imaging positions corresponding to said second operational orientation settings are defined between a range of 35°-50°.

16. The apparatus according to claim 12, wherein the transformation means are arranged for defining a second subset of second operational orientation settings of said imaging means for orientation in said second imaging position, said second subset of second operational orientation settings being conformal to said first operational orientation setting.

17. The apparatus according to claim 12, wherein the transformation means are arranged for determining a longitudinal orientation of said target volume in said first two-dimensional image projection.

18. The apparatus according to claim 17, wherein the transformation means are arranged for selecting said one of said second operational orientation settings to correspond to a second imaging position being defined in a plane perpendicular to said longitudinal orientation of said target volume being determined.

19. The apparatus according to claim 17, wherein for determining said longitudinal orientation of said target volume in said first two-dimensional image projection the transformation means are arranged for defining in said first two-dimensional image projection a first point of interest inside said target volume as well as a second point of interest inside said target volume and for determining said longitudinal orientation of said target volume based on said first and second point of interest.

20. The apparatus according to claim 12, further comprising positioning means for positioning the imaging means in an imaging position and wherein the transformation means are arranged for controlling said positioning means for positioning said imaging means in said second imaging position corresponding to said second operational orientation setting being selected.

21. The apparatus according to claim 12, wherein the imaging means comprise an X-ray imaging device.

* * * * *